United States Patent [19]

Torfs et al.

[11] Patent Number: 4,801,429

[45] Date of Patent: Jan. 31, 1989

[54] AUTOMATIC SAMPLE HANDLING DEVICE

[75] Inventors: Jan C. M. Torfs; Johannes P. M. Laarhoven; Christiaan F. J. Van Heel, all of Terneuzen, Netherlands

[73] Assignee: Dow Nederland B.V., Terneuzen, Netherlands

[21] Appl. No.: 76,525

[22] Filed: Jul. 16, 1987

Related U.S. Application Data

[63] Continuation of Ser. No. 868,394, May 27, 1986, abandoned, which is a continuation-in-part of Ser. No. 580,995, Feb. 16, 1984, abandoned.

[51] Int. Cl.$^4$ .................. G01N 25/00; G01N 35/00
[52] U.S. Cl. ........................................ 422/63; 374/10; 374/12; 414/737; 414/744.3; 414/793; 422/78; 422/80; 422/100
[58] Field of Search ............... 422/51, 63, 64, 65, 422/68, 80, 78, 100, 102; 374/10, 12; 414/627, 637, 752, 737, 744 B

[56] References Cited

U.S. PATENT DOCUMENTS

| | | | |
|---|---|---|---|
| 3,047,933 | 8/1962 | Chick et al. | 414/744 B |
| 3,302,452 | 2/1967 | Leslie | 422/65 |
| 3,504,376 | 3/1970 | Bednar et al. | 422/64 |
| 3,721,352 | 3/1973 | Messmer | 414/627 |
| 3,770,140 | 11/1973 | Dukette | 414/627 |
| 3,934,920 | 1/1976 | Rowekamp | 414/627 |
| 4,368,991 | 1/1983 | Hentze | 374/12 |
| 4,495,149 | 1/1985 | Iwata et al. | 422/67 |

Primary Examiner—Michael S. Marcus
Attorney, Agent, or Firm—Philip D. Shepherd; Jonathan W. Morse

[57] ABSTRACT

A sample handling device for automatically handling a multiplicity of samples, particularly the encapsulated samples for evaluation using a differential scanning calorimeter, on an individual basis. The device comprises a vacuum means, which is capable of transferring a new sample to be substituted for a tested sample, a transfer means, which is capable of removing and replacing a cover means to allow the transfer of the new sample to be substituted for the tested sample.

3 Claims, 3 Drawing Sheets

AUTOMATIC SAMPLE HANDLING DEVICE

CROSS-REFERENCE TO RELATED APPLICATION

This is a continuation of application Ser. No. 868,394, filed May 27, 1986, abandoned which is a continuation-in-part of U.S. application Ser. No. 580,995, filed Feb. 16, 1984 abandoned.

BACKGROUND OF THE INVENTION

The present invention relates to a device for automatically handling a plurality of samples on an individual basis.

A differential scanning calorimeter (DSC) is commonly employed as one method for thermally analyzing a material. Using DSC analysis, the difference in energy fed into a test material and a reference material are measured as a function of temperature, while the test and reference material are subjected, in an environmental (measuring) cell, to a controlled temperature program. In a conventional evaluation, using a DSC, a relatively small, encapsulated sample of the test material is placed in the measuring cell containing a sample of the reference material, and the measuring cell is then covered by a lid having a passageway to allow the escape of gas from the measuring cell. In addition, one or more thermal sleeves and/or protective hoods are generally placed over the measuring cell. Following the thermal evaluation, which generally takes about one hour, the insulating sleeve(s) and/or protective hood(s) are removed from the measuring cell and a new, encapsulated sample to be tested is exchanged for the previously tested sample of the test material.

Heretofore, this periodic sample transfer, a time consuming operation, has been conducted manually. Unfortunately, for various reasons (e.g., the required number of operations and the comparatively small size of the encapsulated sample), no one has been able to successfully automate the sample transfer procedure of a differential scanning calorimeter. For this reason it would be desirable to provide an effective and economical device for handling a number of samples over an extended period of time.

SUMMARY OF THE INVENTION

In one aspect, the present invention is an apparatus for automatically handling a plurality of samples for testing in a thermal analysis device. The basic apparatus comprises a sample holder capable of holding a plurality of samples, a sample receptacle capable of holding for thermal analysis at least one sample, a vacuum unit associated with the sample holder and the sample receptacle, for removing at least one sample from the holder and depositing it in the receptacle, a protector unit for the sample receptacle, a transfer means associated with the protector unit, for removing and replacing the protector unit on the sample receptacle. The apparatus also includes a control system which, in a cycle of operation, (1) activates the vacuum unit, to remove at least one sample from the holder, carry it to the receptacle, and deposit it in the receptacle, (2) activates the transfer means, to place the protector unit on the receptacle, (3) activates the transfer means, to remove the protector unit from the receptacle, (4) activates the vacuum unit, to remove the sample(s) from the receptacle, carry the sample(s) away from the receptacle, and drop the sample(s) at a desired location.

In a preferred embodiment, the transfer means is a vacuum means. In said embodiment, a preferred protector unit is designed such that gases can freely pass to or from the receptacle, but a vacuum can effectively be applied to the cover. A preferred cover means for the receptacle comprises a disk or sheet having one or more perforations or passages which allow the flow of gas from one surface of the disk or sheet to the opposite surface and a continuous disk or sheet which allows essentially no gas to flow through it. The perforated disk or sheet, and the continuous disk or sheet, are connected by a conduit having one or more perforations or passages, such that gas passing through the perforated disk or sheet subsequently passes from the conduit through said perforations or passages.

In another embodiment, the protector unit includes an insulating sleeve and protective hood conventionally employed in combination with the DSC cell, and they are preferably designed so that, upon their removal to allow sample transfer, the insulating sleeve can be placed in a receptacle, preferably a tapered receptacle, formed from or fixed to the top of the protective hood and the cover means can be placed in a container formed from or fixed to the top of the insulating sleeve. In such a manner, removal and replacement of the protective hood, insulating sleeve and cover means can be conducted using a minimum of movable apparatus.

The apparatus of this invention is unique, in that it provides an effective and economical means for automatically transferring, in a systematic order, the relatively small, encapsulated samples used for thermal analysis, such as by DSC, or similar evaluation techniques. Moreover, the complexity of the equipment required to provide such automatic samples transfer is surprisingly small. For example, lifting of the relatively small encapsulated samples, as well as the comparatively larger and heavier cover means, insulating sleeve, and protective hood, for subsequent movement can be accomplished using one vacuum, thereby requiring a single source of vacuum. In addition, the movement, i.e., removal and replacement, of the small, encapsulated sample and the cover means, insulating sleeve, and protective hood, can be conducted using air-driven pistons and a single source of compressed air.

The apparatus is useful for automatically handling experimental and unattended evaluation of a plurality of samples over an extended period. The apparatus and method are particularly useful in conjunction with conventional DSC type equipment, including both the power compensation DSC and the heat flux DSC.

DESCRIPTION OF THE DRAWINGS

Understanding of this invention will be facilitated by referring to the accompanying drawings, in which.

DESCRIPTION OF THE INVENTION

Figure 1:
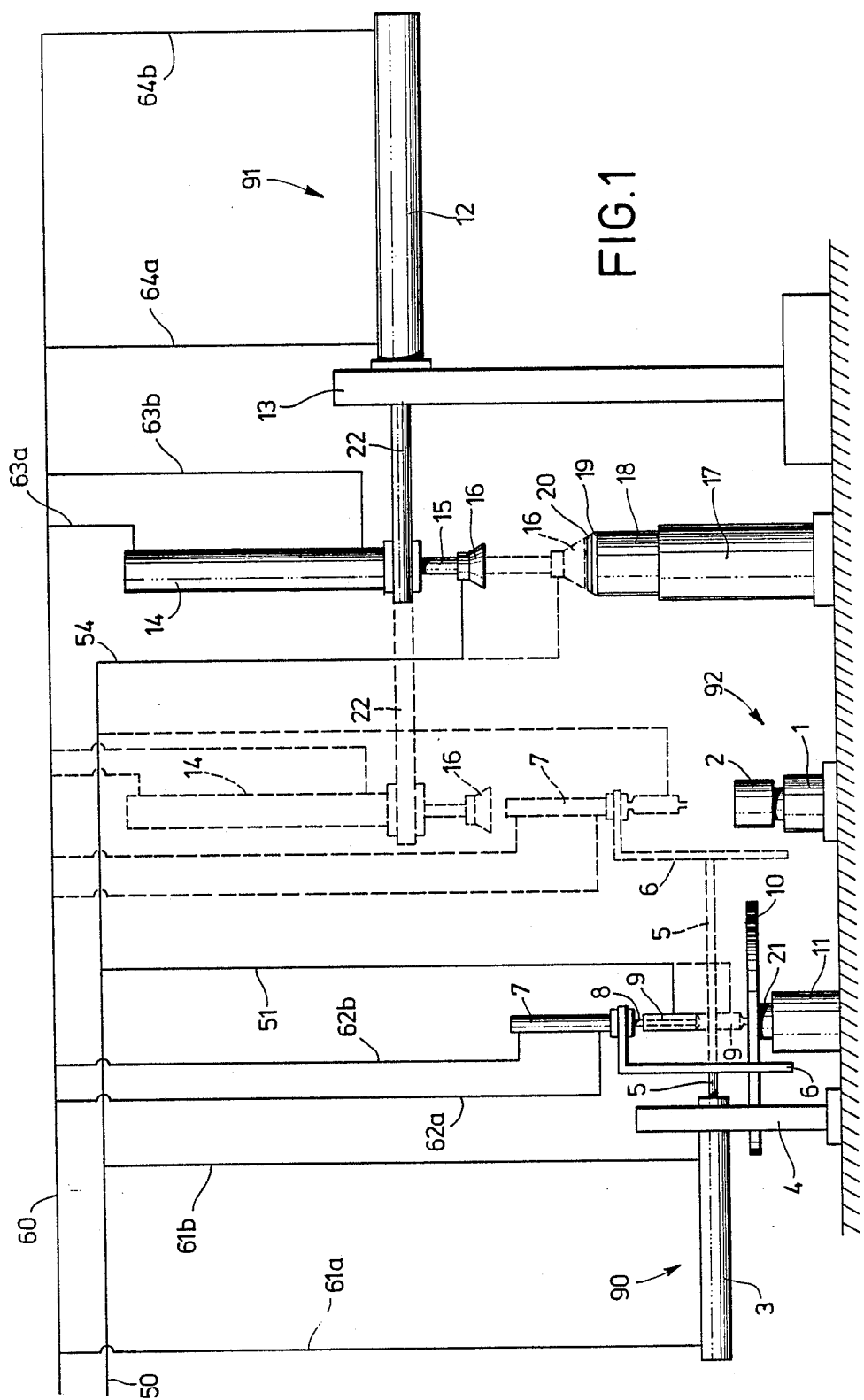
FIG. 1 is a schematic representation that illustrates an embodiment of the present invention wherein the apparatus of the present invention is employed in conjunction with a DSC.

Referring now more particularly to the drawings, FIG. 1, which represents an embodiment of the present invention, depicts a differential scanning calorimeter cell 92 having a support 1 and a receptacle 2. A first vacuum means 90, for transferring samples of the materials to be tested from a sample holder, such as sample table 10, to the receptacle 2 of measuring cell 92 and for removing tested samples therefrom, comprises a first air cylinder 3, which is supported by stand 4 and connected to a source of air (not shown) by means of lines 61a and 61b. Cylinder 3 has a slidable piston or rod 5 connected to a movable support 6. Movable support 6 supports a second air cylinder 7. Second air cylinder 7 is connected to the source of air by means of lines 62a and 62b. A vacuum nozzle 9 is connected to cylinder 7 by a slidable piston or rod 8. Vacuum nozzle 9 is connected to a source of vacuum (not shown) by means of line 51.

The sample table 10 is mounted on a base 11 and it rotates by means of rotating rod or bearing 21. The table 10 and nozzle 9 are positioned such that vacuum nozzle 9 can pick up a sample from table 10 and transport it to the receptacle 2 of the DSC unit.

The sample handling apparatus illustrated in FIG. 1 further comprises a second vacuum means 91 having a third air-driven cylinder 12 supported by stand 13 and connected to an air source by means of lines 64a and 64b. Associated with cylinder 12 is a slidable piston or rod 22, which supports a fourth air-driven cylinder 14. Cylinder 14 is connected to air source by means of lines 63a and 63b. Associated with cylinder 14 is a slidable piston or rod 15 having a vacuum cup 16 connected thereto. Vacuum cup 16 is connected to the source of vacuum by line 54.

In the embodiment shown in FIG. 1, means for enclosing the receptacle 2 of the DSC cell 92 (i.e., protector unit) comprises a cover means 20, insulating sleeve 18, and protective hood 17. Cover means 20 is shown to rest in a container 19, which is permanently fixed to insulating sleeve 18. In turn, insulating sleeve 18 rests on the protective hood 17.

During each cycle of operation of this apparatus, the tested sample is removed from receptacle 2 by extending the slidable piston 5, associated with first cyclinder 3, such that the second cylinder means 7 and the vacuum nozzle 9 are positioned directly over the open receptacle 2 of the DSC cell 92. Slidable piston 8 is then extended until nozzle 9 contacts the encapsulated sample of the tested material within the receptacle 2. A vacuum is created in nozzle 9 by means of line 51, which allows the sample to be withdrawn from the receptacle upon the return of piston 8 towards its original position. Piston 5 is thereafter returned to its original, unextended position. During its return, the vacuum in nozzle 9 is interrupted briefly to allow the tested sample to drop harmlessly therefrom. Preferably, the sample is dropped in a desired location where the samples are held in the order in which they are dropped. More preferably, there is an associated detector means which will react if there is no sample dropped during a cycle of operation or if no sample is removed from the receptacle. In this way the analysis device can automatically stop or sound an alarm if the sample becomes lodged in the receptacle during analysis and was not removed by the vacuum unit.

An encapsulated sample of an untested material to be exchanged for the just removed sample of tested material is removed from sample table 10 by extending piston 8 to allow the nozzle 9 to contact the untested sample on table 10. The vacuum existing in nozzle 9 allows the removal of the encapsulated sample from table 10 upon the return of piston 8 to its original position.

To place the sample of the untested material in the receptacle 2 of the measuring cell 92, piston 5 is again extended such that second cylinder means 7 and vacuum nozzle 9 are properly positioned directly over the open receptacle 2 of DSC cell 92. At the completion of such extension, nozzle 9, still carrying the untested sample, is lowered into the receptacle by extension of piston 8. The vacuum existing in nozzle 9 is then ceased. Piston 8 is then returned without the sample to its original position, leaving the encapsulated sample of the untested material positioned in its proper location within receptacle 2. Subsequently, piston 5 is also returned to its original, unextended position.

Prior to testing of the newly positioned sample, the cover means 20, insulating sleeve 18 and protective hood 17 are placed over the receptacle 2 of the DSC cell 92. The cover 20 is replaced by extending piston 15 such that the vacuum cup 16 contacts the cover means. A vacuum is generated in vacuum cup 16 by means of line 54 sufficient to lift the cover from the container 19 upon return of piston 15 to its original, unextended position. Cover 15 is subsequently placed over the receptacle 2 by extending piston means 22 such that the cylinder 14 and piston 15 are properly positioned directly over the DSC cell 92. Subsequently, piston means 15 is extended, hereby lowering the cover means 20 in the receptacle 2. The vacuum in the vacuum cup is subsequently terminated. The piston 15 and vacuum cup 16 are returned to their original, unextended position, leaving the cover means 20 in its proper location in receptacle 2. The piston 22 is then returned to its original, unextended position.

The insulating sleeve 18 and protective hood 17 are placed over the receptacle 2 following a similar procedure. Specifically, the piston 15 is extended such that the vacuum cup 16 contacts the insulating sleeve 18 or the container 19 affixed thereto such that upon return of the piston to its original position, the insulating sleeve is carried by the vacuum cup. The piston 22 is then extended to a proper position over the DSC cell. Subsequently, the piston 15 is extended to place the insulating sleeve over the receptacle 2 of the DSC cell 92. The vacuum to the vacuum cup 16 is then terminated and the pistons 15 and 22 returned to their original, unextended positions.

The protective hood 17 is then placed over the DSC cell by picking up the protective hood 17 from its rest position by means of piston 15 and vacuum cup 16. Thereafter, piston 22 is extended to properly position the protective hood 17 over the DSC cell. The piston 15 is then extended and the vacuum of vacuum cup 16 released, leaving the hood 17 covering the DSC cell 92. The pistons 15 and 22 are then returned to its extended position. The protective hood, insulating sleeve and cover means are easily removed from the DSC cell by performing the above-described steps in a reversed order.

Although the illustrated embodiment depicts the use of vacuum, which is generally preferred in the application of the present invention, to transfer the protector unit, including cover means as well as any insulating sleeve(s) or protective hood(s), the transfer means can also suitably comprise a magnet (if the cover, sleeve and/or hood are of a suitable material) or the like for conducting the described transfer.

During each cycle of the hereinbefore described operation, the sample holder and/or first vacuum means operate such that an encapsulated sample of a new, untested material is capable of being provided to the receptacle of the DSC cell during the following cycle of operation. Any of a variety of methods can be employed to assure that a new sample is transferred from the sample holder to the DSC cell during each cycle of operation. Of such methods, one preferred method consists of rotating the sample table 10 during each cycle so as to position a new sample under vacuum nozzle 9 following each cycle of operation. A preferred sample table 10 and carrier support 6 which provide such movements are depicted in FIGS. 2 and 3.

Figure 2:
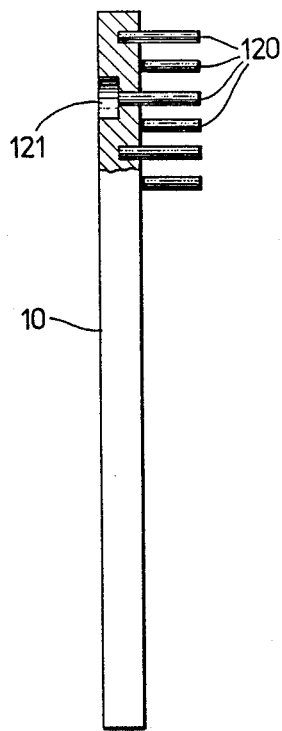
FIG. 2 is a side view schematic representation, partly in cross-section, of a preferred sample holder.
Figure 3:
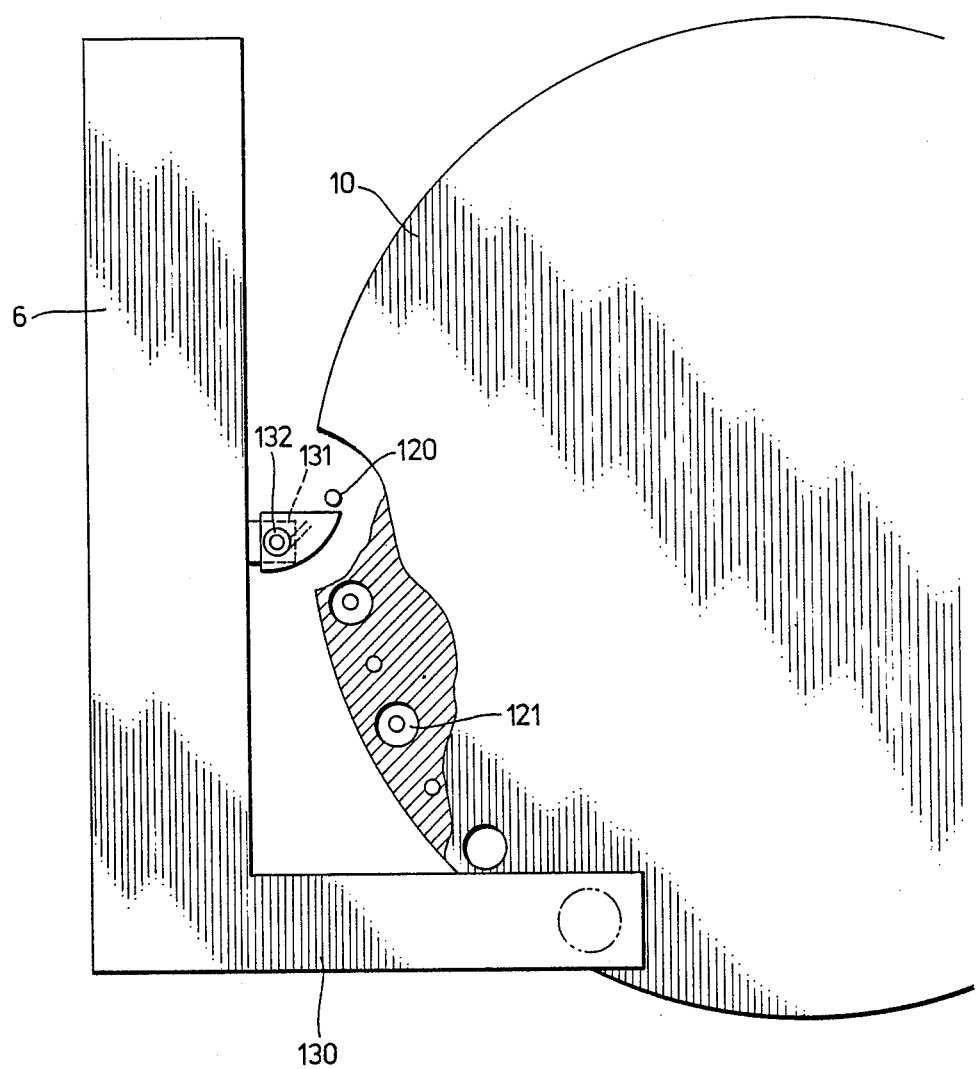
FIG. 3 is a top view schematic isometric representation of the sample table illustrated in FIG. 2, and further depicting a means for moving the sample holder to insure a new sample is tested following each cycle.

Specifically, FIGS. 2 and 3 depict a round sample table useful in the embodiment depicted in FIG. 1. The illustrated sample table preferably comprises a multiplicity of equidistant sample receptacles 121 which form a circle having the same center or essentially the same center as table 10. The size of table 10 is primarily selected on the maximum number of samples to be tested prior to operator intervention. Typically, the table contains sufficient sample receptacles so that the operation can be conducted overnight without the necessity of an operator being present, i.e., the table will conventionally hold a sufficient number of samples to provide a continuous operation of at least 16 hours. As illustrated, a series of permanently affixed, catch pins 120 extend in a circle around the center of sample table 10. In the illustrated embodiment, there are twice as many catch pins extending from table 10 as sample receptacles contained by the table and each of the pins is spaced equidistant from the two adjacent catch pins.

FIG. 3 depicts, in more detail, the sample table and the means for moving the sample table such that an untested sample is made available for placement in the receptacle of the DSC cell during each cycle of operation. Specifically, FIG. 3 depicts the carrier support 6 having support arm 130 for supporting cylinder 7. At or near the base of carrier support 6, is a spring loaded, movable trigger 131. In operation, the interaction of the movable trigger 131 of carrier support 6, with the catch pins 120 extending from table 10 causes the rotation of sample table 10 in a manner sufficient to provide a new encapsulated sample during each cycle of operation.

Specifically, as a new sample is being transported to receptacle 2, the trigger 131 of carrier support 6 catches one catch pin 120 in a manner such that table 10 rotates one half the distance required to place a new sample under vacuum nozzle 9. When the carrier support is returned to its original position, there is no movement in the sample table 10 upon contact of trigger 131 and a catch pin 120 due to the partial rotation of trigger 131 around the catch pin. Once contact between pin 120 and trigger 131 is terminated, trigger 131 is brought to its original position by spring 132. When piston 5 is extended for the removal of the tested sample from the DSC cell, the contact of trigger 131 with catch pin 120 rotates the sample table 10 sufficiently to place the new sample directly under nozzle 9.

Again, upon the return of piston 5 to its unextended position the spring loading of trigger 131 provided no additional rotation of the table upon the contact of catch pin 120 and trigger 131. In the described manner, the sample table is removed in a manner such that the vacuum nozzle 9 is now capable of transferring a new sample of an untested material to the differential scanning calorimeter cell during each cycle of operation. This technique merely illustrates one method for insuring a new sample is available during each cycle of the sample handling device and should not be construed to limit the scope of the present invention.

Figure 4:
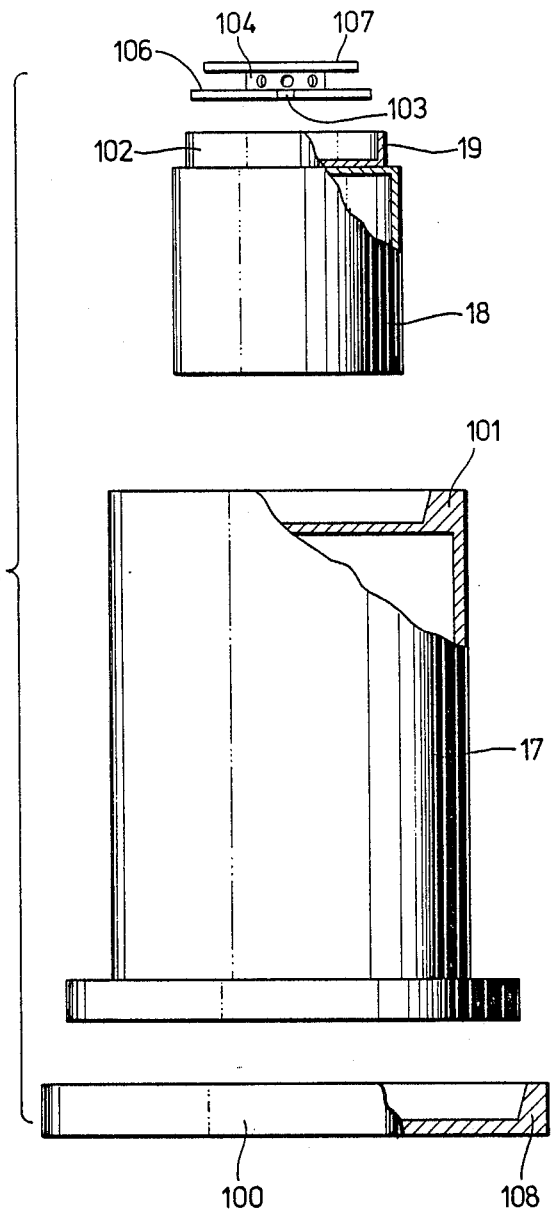
FIG. 4 is a detailed schematic representation, partly in cross-section, of a protector unit comprising cover means, insulating sleeve and protective hood for enclosing the measuring cell of the DSC depicted in FIG. 1.

With regard to the other components useful in this invention, FIG. 4 depicts a preferred protector unit comprising cover means, insulating sleeve, and protective hood. The preferred cover means 20 comprises a gas permeable disk or plate 106, said permeability allowing for the passage of gases through plate or disk 106 and a continuous plate or disk 107 which is essentially impermeable to the passage of gas therethrough. Permeable plate 106 and non-permeable plate 107 are connected or joined by means of a permeable conduit 104 which allows the passage of gas from the interior of the conduit to the environment. In the illustrated embodiment, gases flowing through the passage(s) or perforation(s) in plate 106 can flow through the passage(s) or perforation(s) in the conduit 104.

In such manner, during the evaluation of the sample material, any generated gases are free to escape from the receptacle containing the sample, thereby preventing an excessive pressure buildup therein. In addition, a controlled atmosphere can be maintained within the receptacle by purging the cell using a suitable purge gas. Moreover, since top plate 107 is essentially impermeable to the passage of gas, a vacuum can be effectively applied to the top surface thereof and not be readily dissipated. Therefore, the cover means is easily moved by the vacuum cup 16 during the removal and replacement operations.

Insulating sleeve 18 is shown with a container 19 affixed thereto. Container 19 has space provided for receiving the cover means 20 upon its removal from the measuring cell 92. Similarly, the protective hood 17 has a receptacle 101 for receiving insulating sleeve 18. The receptacle 101, as depicted in FIG. 4, is advantageously tapered and conforms to the shape of the insulating sleeve 18. A receiving ring 100, such as depicted in the embodiment illustrated in FIG. 4, for receiving hood 17 upon its removal from around the DSC cell is also advantageously employed herein. Receiving ring 100 comprises a receptacle 108, which is preferably tapered and conforms to the shape of the protective hood 17. The described receptacles 119, 101 and 100 assure proper placement of the cover means, insulating sleeve and protective hood upon their sequential removal from the DSC cell, thereby insuring continuous and repeatable performance of the sample handling device.

The cylinders 3, 7, 12 and 14 are air-activated and, where necessary to dampen vibration, supplemented by the presence of oil. Preferably, each cylinder is capable of being activated by a single source of air. In operation, while each movement of the air-driven cylinders and the application or termination of vacuum, as required, to the vacuum nozzle or vacuum cup can be conducted manually, the advantages of the present invention are recognized when the movement of the cylinders and vacuum control are regulated by a supervisory control system. Supervisory control systems and techniques for using same are well known in the art and reference is made thereto for the purposes of this invention. Pneumatic valves operated in combination with microprocessor control have been found to be particularly useful in the operation of the automatic sample handling device as illustrated in FIG. 1.

The vacuum nozzle 9 and vacuum cup 16 are designed such that, at the same vacuum, vacuum nozzle 9 is capable of transporting the encapsulated sample without significant damage occurring thereto and vacuum cup 16 is capable of securely transporting the cover means, insulating sleeve and protective hood. The nozzle 9 and vacuum cup 16 illustrated in the Figures are merely representative of a design that can be suitably employed herein. Vacuum nozzles and/or cups of design capable of performing the same function are also suitably employed herein.

The invention claimed is:

1. An apparatus for automatically handling a plurality of samples for testing in a thermal analysis device, which comprises:
   a sample holder capable of holding a plurality of samples;
   a sample receptacle capable of holding for thermal analysis at least one sample;
   a vacuum unit associated with the sample holder and the sample receptacle, for removing at least one sample from the sample holder, depositing the sample(s) in the sample receptacle, and removing the sample(s) from the sample receptacle;
   a protector unit for the sample receptacle, the unit comprising a cover means, an insulating sleeve, and a protective hood;
   a transfer means associated with the protector unit, and adapted to hold, place and remove said cover means, said insulating sleeve, and said protective hood; and
   a control system which, in a cycle of operation:
     (1) activates the vacuum unit, to remove at least one sample from the sample holder, carry the sample to the sample receptacle, and deposit the sample in the receptacle;
     (2) activates the transfer means, to place the protector unit on the sample receptacle;
     (3) activates the transfer means, to remove the protector unit from the receptacle; and
     (4) activates the vacuum unit, to remove the sample(s) from the receptacle, carry the sample away from the receptacle, and drop the sample at a desired location.

2. The apparatus of claim 1 in which the cover of the protector unit is a perforated disk and a continuous disk, which are connected by a perforated conduit, such that gas can flow through the perforated disk, but cannot flow through the continuous disk, and after the gas flows through the perforated disk it flows through the perforations in the conduit.

3. The apparatus of claim 1 in which the transfer means is a vacuum unit.

* * * * *